United States Patent [19]

Woltersdorf, Jr. et al.

[11] Patent Number: 4,769,370

[45] Date of Patent: Sep. 6, 1988

[54] (1,2-DICHLORO-8-OXO-5A-SUBSTITUTED-5A,6,7,8-TETRAHYDRODIBENZOFURAN-3-YL)ALKANOIC ACIDS AND ALKANIMIDAMIDES

[75] Inventors: Otto W. Woltersdorf, Jr., Chalfont; Edward J. Cragoe, Jr., Lansdale, both of Pa.

[73] Assignee: Merck & Co., Inc., Rahway, N.J.

[21] Appl. No.: 910,922

[22] Filed: Sep. 24, 1986

[51] Int. Cl.$^4$ .................... A61K 31/34; C07D 307/91
[52] U.S. Cl. .................... 514/256; 514/320; 514/402; 514/422; 514/468; 544/333; 546/196; 548/348; 548/525; 549/460
[58] Field of Search .......... 549/460; 544/333; 546/196; 548/348, 525; 514/256, 320, 402, 422, 468

[56]  References Cited

U.S. PATENT DOCUMENTS

| 4,316,043 | 2/1982 | Cragoe et al. | 560/53 |
|---|---|---|---|
| 4,317,922 | 3/1982 | Cragoe et al. | 562/461 |
| 4,337,354 | 6/1982 | Cragoe et al. | 562/461 |
| 4,356,313 | 10/1982 | Cragoe et al. | 560/53 |
| 4,356,314 | 10/1982 | Cragoe et al. | 560/53 |
| 4,389,417 | 6/1983 | Bourke et al. | 424/317 |
| 4,394,385 | 7/1983 | Cragoe | 514/468 |
| 4,463,208 | 7/1984 | Cragoe et al. | 562/462 |
| 4,465,850 | 8/1984 | Cragoe et al. | 560/53 |
| 4,579,869 | 4/1986 | Cragoe et al. | 562/456 |
| 4,604,396 | 8/1986 | Cragoe et al. | 514/256 |

OTHER PUBLICATIONS

J. Med. Chem. (1982) Cragoe, et al. 25 pp. 567-679.
J. Med. Chem. (1986) Cragoe, et al. 29 pp. 825-842.

Primary Examiner—Mary C. Lee
Assistant Examiner—Bernard I. Dentz
Attorney, Agent, or Firm—Charles M. Caruso; Hesna J. Pfeiffer

[57]  ABSTRACT

The invention relates to novel (1,2-dichloro-8-oxo-5a-substituted-5a,6,7,8-tetrahydrodibenzofuran-3-yl)alkanoic acids and alkanimidamides, their derivatives and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections including that due to AIDS virus, various brain concussions and elevated intracranial pressure.

13 Claims, No Drawings

(1,2-DICHLORO-8-OXO-5A-SUBSTITUTED-5A,6,7,8-TETRAHYDRODIBENZOFURAN-3-YL)ALKANOIC ACIDS AND ALKANIMIDAMIDES

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections, AIDS virus, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

Two recent publications, one entitled "*Agents for the Treatment of Brain Injury*" 1. (Aryloxy)alkanoic Acids, by Cragoe et al, J. Med. Chem., (1982) 25, 567–579 and the other, "*Agents for the Treatment of Brain Edema* 2. [(2,3,9,9a-tetra-hydro-3-oxo-9a-substituted-1H-fluoren-7-yl)-oxy]alkanoic Acids and Their Analogs*", by Cragoe et al, J. Med. Chem., 29, 825–841 (1986), report recent experimental testing of agents for treatment of brain injury and review the current status of treatment of brain injury. Additionally, U.S. Pat. Nos. 4,316,043, 4,317,922, 4,337,354, 4,356,313, 4,356,314, 4,389,417, 4,394,385, 4,463,208, 4,465,850, 4,579,869, and 4,604,396 disclose certain alkanoic acids, cycloalkanoic acids or their amidine analogs for the treatment of grey matter edema.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

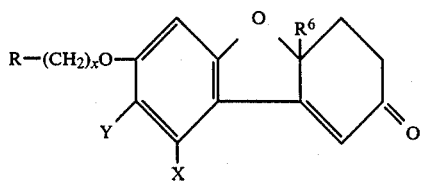

wherein:
R is

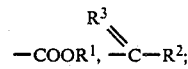

$R^1$ is hydrogen, $C_1$–$C_6$ alkyl, $C_1$–$C_6$ carboxyalkyl;
$R^2$ is $NH_2$, $NHR^4$ or $NR^4R^5$;
$R^3$ is $NH_5$ or $NR^5$;
$R^4$ and $R^5$ are each independently lower alkyl, branched or unbranched, containing from 1 to 5 carbon atoms, or amino, provided that $R^4$ and $R^5$ are not both amino;
wherein $R^2$ and $R^3$ may be joined together via $R^4$ to form a heterocyclic ring of 5 or 6 atoms containing 2 nitrogen atoms and 3 or 4 carbon atoms, such as

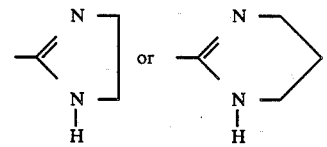

or wherein $R^4$ and $R^5$ may be joined together to form a 5- or 6-membered ring containing one nitrogen atom and 4 or 5 carbon atoms, such as:

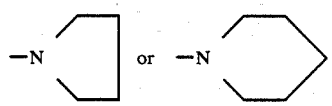

$R^6$ is lower alkyl, branched or unbranched, containing from 1 to 5 carbon atoms such as methyl, ethyl, n-propyl, isopropyl and the like, aryl such as phenyl, halo substituted aryl such as p-fluorophenyl, o-fluorophenyl, p-chlorophenyl and the like, aralkyl such as benzyl, cycloalkyl containing from 3 to 6 nuclear carbon atoms such as cyclopropyl, cyclobutyl, cyclopenyl and the like, or cycloalkyl-lower alkyl containing from 4 to 7 total carbon atoms such as cyclopentylmethyl.

X and Y are halo or lower alkyl, such as methyl; and x is 1 to 4.

Since the 5a-carbon atom in the molecule is asymmetric, the compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Since the ethaneimidamide products of the invention are basic, the invention also includes the obvious pharmaceutically acceptable acid addition salts such as the hydrochloride, hydrobromide, sulfate, isethionate, acetate, methanesulfonate, maleate, succinate and the like salts.

Likewise, since the alkanoic acid products of the invention are acidic, the invention also includes the obvious pharmaceutically acceptable salts such as the sodium, potassium, ammonium, trimethylammonium, piperazinium, 1-methylpiperazinium, guanidinium, bis-(2-hydroxyethyl)ammonium, N-methyl-glucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel (1,2-dichloro-8-oxo-5a-substituted-5a,6,7,8-tetrahydrodibenzofuran-3-yl)alkanoic acids and alkanimidamides, and their salts, it also includes their derivatives, such as oximes, hydrazones, esters and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

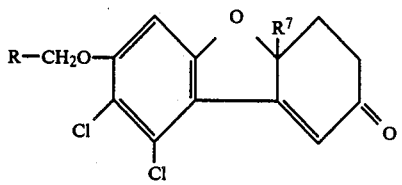

wherein: R is carboxy,

$R^7$ is lower alkyl, branched or unbranched, containing from 1 to 5 carbon atoms.

A preferred compound is [(1,2-dichloro-8-oxo-5a-propyl-5a,6,7,8-tetrahydrodibenzofuran-3-yl)oxy]acetic acid.

Also preferred is 1-carboxy-1-methylethyl [(1,2-dichloro-8-oxo-5a-propyl-5a,6,7,8-tetrahydrodibenzofuran-3-yl)oxy]acetate.

Also preferred is 2-[(1,2-dichloro-8-oxo-5a-propyl-5a,6,7,8-tetrahydrodibenzofuran-3-yl)oxy]ethanimidamide hydrochloride.

Especially preferred are the pure enantiomers since, in most instances, one enantiomer is more active biologically then its antipode.

Included within the scope of this invention are the pharmaceutically acceptable salts of (1,2-dichloro-8-oxo-5a-substituted-5a,6,7,8-tetrahydrodibenzofuran-3-yl) alkanoic acids and alkanimidamides since a major medical use of these compounds is solutions of their soluble salts which can be administered parenterally.

Thus, the acid addition salts can be prepared by the reaction of the (1,2-dichloro-8-oxo-5a-substituted-5a,6,7,8-tetrahydrodibenzofuran-3-yl)alkanoic acids of this invention with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methylpiperazine, guanidine, bis-(2-hydroxyethyl)amine, N-methyl-glucosamine and the like salts of the alkanimidamides of this invention may be prepared by reaction with an appropriate pharmaceutically acceptable mineral acid or organic carboxylic acid, such as hydrochloric acid, sulfuric acid, hydrobromic acid, isethionic acid, methanesulfonic acid, maleic acid, succinic acid, acetic acid and the like. The salts selected are derived from among the non-toxic, pharmaceutically acceptable acids.

The synthesis of the compounds of this invention in which R=COOH and x=1 (Ia) is illustrated by the following nine-step series of reactions to produce IIa wherein R=COOH, X=1, and $R^7$=propyl.

SCHEME I

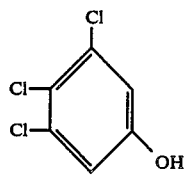

(III)

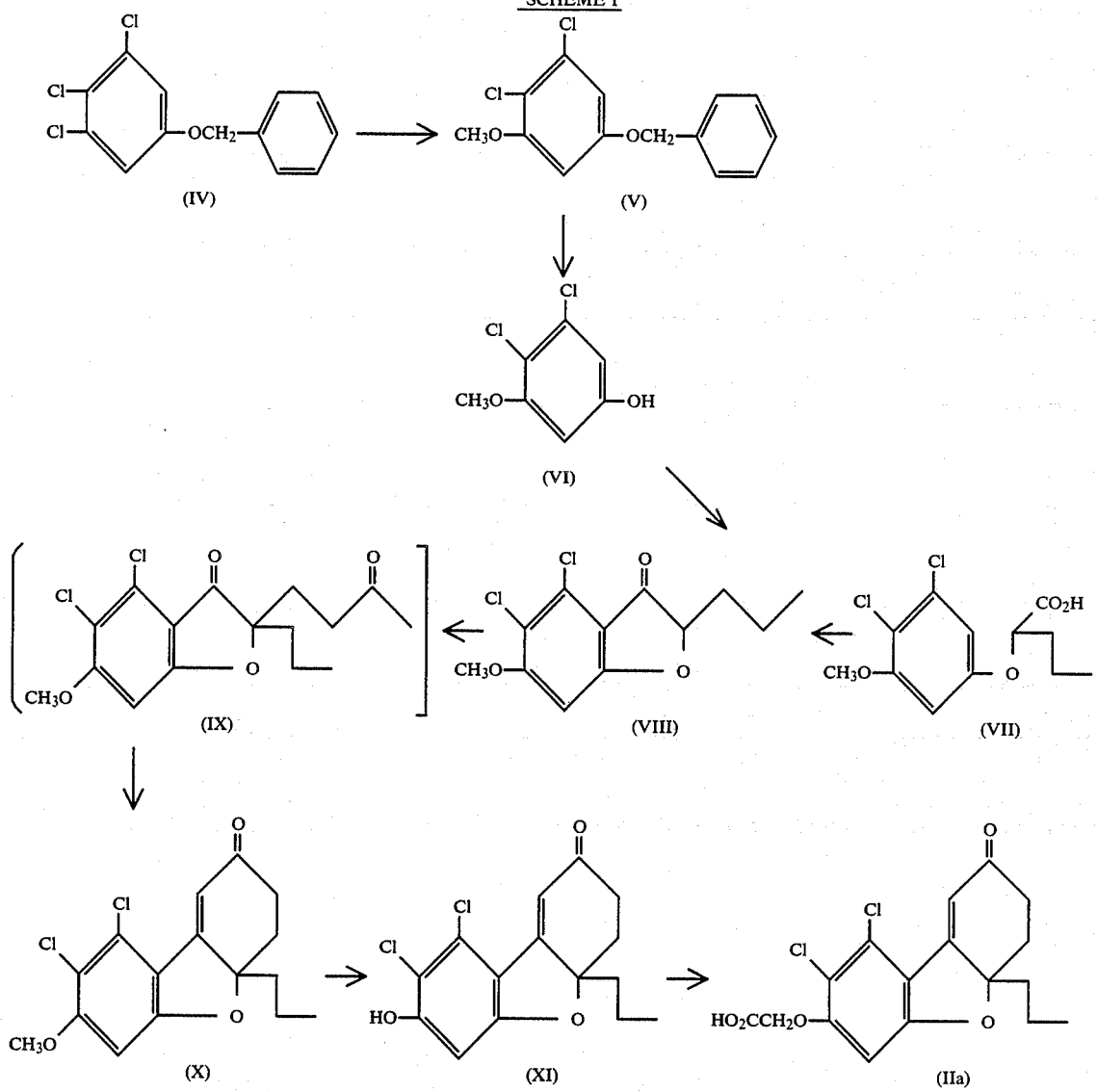

The phenol of Formula III is reacted with benzyl bromide in the presence of a base, such as potassium carbonate using a solvent, such as N,N-dimethylformamide. The reaction is completed by stirring and heating at 40°–80° C. for 1 to 6 hours. Methoxylation of the compound of Formula IV to the anisole of Formula V occurs by heating with sodium methoxide in a solvent like hexamethylphosphoramide. The reaction requires stirring and heating at 80° to 120° C. for 15–25 hours. Cleavage of the benzyl moiety of the compound of Formula V to give the compound of Formula VI results by reaction with hydrogen in the presence of a catalyst, such as 5% palladium on carbon.

The reaction requires shaking in a hydrogen atmosphere at 20 to 30 p.s.i at a temperature of 20–30° C. for 2–5 hours.

Treatment of the compound of Formula VI with ethyl 2-bromopentanoate in N,N-dimethylformamide at 50° to 75° C. for 30 minutes to 2 hours produces the ethyl ester corresponding to Formula VII. Hydrolysis of this ester in aqueous sodium hydroxide and N,N-dimethylformamide by heating and stirring at 80°–100° C. for 3 to 6 hours produces the compound of Formula VII upon acidification. Annulation of the compound VII to form compound VIII is accomplished by first converting the compound of Formula VII to the corresponding acid chloride. This is accomplished by reaction with thionyl chloride in benzene at reflux for about one hour. The annulation to compound VIII is then effected by treatment of the acid chloride with aluminum chloride under Friedel Crafts reaction conditions. The reaction is conducted in methylene chloride, adding the aluminum chloride at 0°–10° C. followed by stirring at 20°–30° C. for 15–20 hours and finally refluxing the mixture for 15 minutes to 2 hours.

Reaction of the compound of Formula VIII with methyl vinyl ketone in tetrahydrofuran occurs by heating at 50°–60° C. in the presence of a catalyst, such as 1,5-diazabicyclo[4.3.0]non-5-ene (DBN) or 1,8-diazabicyclo[5.4.0]undec-7-ene (DBU) produces the 2-(3-oxobutyl) derivative (Formula IX). This compound is cyclized by heating in aqueous ethanol containing a catalytic quantity of a strong base such as sodium hydroxide or potassium hydroxide to produce the compound of Formula X.

Cleavage of the methyl ether moiety of the compound of Formula X to form the corresponding phenol of Formula XI is accomplished by heating with molten pyridine hydrochloride at 175° to 195° C. for 15 to 30 minutes. Alternatively, one may use sodium nitrite in N,N-dimethylformamide at 130°–150° C. for 18 to 30 hours.

Reaction of the compound of Formula XI with ethyl bromoacetate in N,N-dimethylformamide at 50°–75° C. for 1 to 3 hours in the presence of a base such as potassium or sodium carbonate produces the ethyl ester corresponding to the compound of Formula IIa. Saponification of this ester is accomplished by heating in aqueous methanolic base such as sodium or potassium hydroxide. The reaction occurs at a temperature of 15° to 50° C. for 15 minutes to 5 hours. The compound of Formula IIa is generated by acidification of the reaction mixture with an acid such as hydrochloric or sulfuric acid.

It is to be recognized that these compounds of Formula I possess an asymmetric carbon atom at position 5a and, therefore, consist of racemates composed of two enantiomers. The resolution of the two enantiomers where R=COOH (Ia) may be accomplished by forming a salt of the racemic mixture with an optically active base such as (+) or (−) amphetamine, (−) cinchonidine, dehydroabietylamine, (+) or (−)-α-methylbenzylamine, (+) or (−)-α-(1-naphthyl)ethylamine, (+) cinchonine, brucine or strychnine and the like in a suitable solvent such as methanol, ethanol, 2-propanol, benzene, acetonitrile, nitromethane, acetone and the like. There is formed in the solution two diastereomeric salts, one of which is usually less soluble in the solvent than the other. Repetitive recrystallization of the crystalline salt generally affords a pure diastereomeric salt from which is obtained the desired pure enantiomer. The optically pure enantiomer is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

Since the products of Formulas Ia and IIa of the invention are acidic, the invention also includes the obvious pharmaceutically acceptable salts, such as the sodium, potassium, ammonium, trimethylammonium, piperazinium, 1-methylpiperazinium, guanidinium, bis-(2-hydroxethyl)ammonium, N-methylglucosammonium and the like salts.

The synthesis of the alkanimidamides of Formula I can be illustrated by the synthesis of IIb wherein

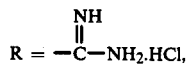

x=1, and $R^6$=propyl which is prepared following two-step reaction

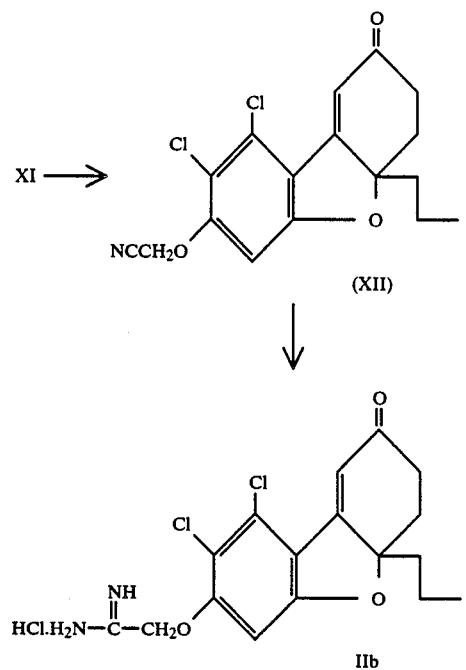

The phenol of Formula XI is reacted with chloroacetonitrile in a base, such as potassium or sodium carbonate and a solvent such as N,N-dimethylformamide. The reaction mixture is heated at 55°–75° C. for 1–5 hours. Treatment of the nitrile of Formula XII with methanol containing a catalytic amount of base, such as sodium or potassium methoxide produces the corresponding imido ester which upon reaction with ammonium chloride produces the compound of Formula IIb.

The pure enantiomers of Formula Ib are conveniently prepared from the pure enantiomer of Formula Ia which in turn are converted to the pure enantiomeric phenols (XI), nitriles (XII) and alkanimidamides (Ib). This is illustrated by the series of reactions to produce IIb-R and IIb-S from Ia-R and Ib-S:

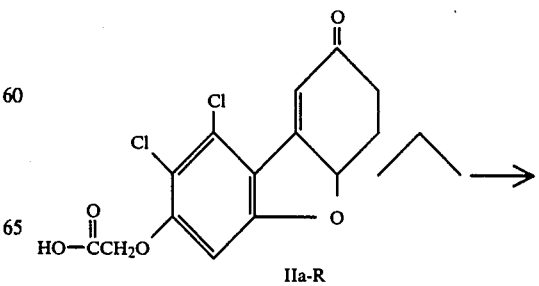

-continued

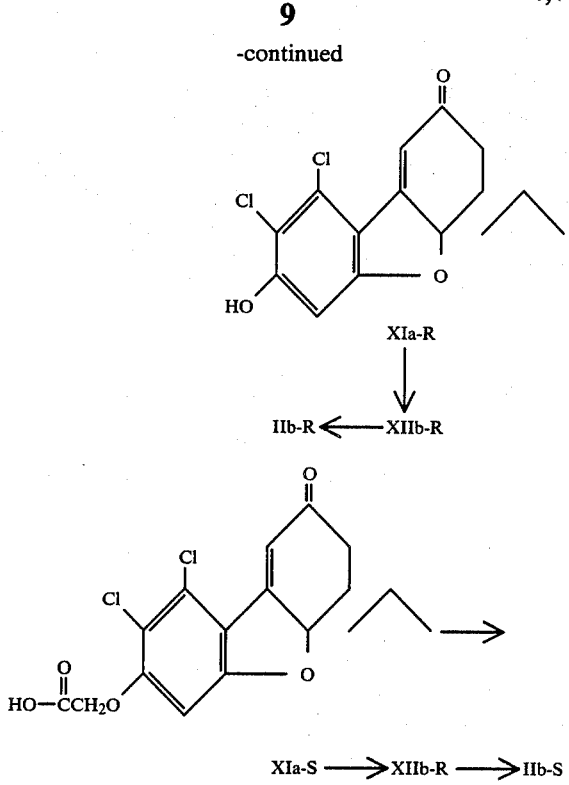

The acid addition salts of Formula Ib or IIb are formed by at least one of two methods. (1) The salt of ammonia or amine used in the reaction of the imido ester generated from the compound of Formula XII determines the salt of Formula Ib or IIb. (2) The salt of Formula Ib or IIb can be converted to the free base by treatment with aqueous base, such as sodium or potassium hydroxide) and the free base treated with a pharmaceutically acceptable acid, for example mineral acids, carboxylic acids or other organic acids, such as hydrochloric acid, sulfuric acid, isethionic acid, methanesulfonic acid, tartaric acid, succinic acid, maleic acid, acetic acid and the like.

The reaction may be conducted in water but it is preferred to conduct the reaction in an organic solvent, such as ether, ethanol, N,N-dimethylformamide and the like.

The preferred salts are the pharmaceutically acceptable salts such as the hydrochloride salts and the like.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions and elevated intracranial pressure, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or position emission tomography (PET) scans of the brain. The sum of the neurological evaluation is presented in the Glasgow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 20 mg/kg of body weight as a single dose, preferably from 0.2 mg/kg to 10 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1.5 to 2 times the initial dose every 4 to 24 hours. For example, 3 intravenous doses of 4, 6 and 8 mg/kg of body weight can be given at 6 hour intervals. If necessary, 4 additional doses of 8 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhanc the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. August 29-31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R. ; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, c.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V.; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention can be tested for activity. This test provides the principal in vitro evaluation and consists of a determination of concentration vs. response curve. The addition of $HCO_3^-$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-response curves are then obtained. The data are expressed as percent $HCO_3^-$-stimulated swelling vs. drug concentration, from which the concentration of drug providing 50% inhibition of $HCO_3^-$-stimulated swelling ($I_{50}$ in molarity) is interpolated.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims. All temperatures in the examples are in Centigrade unless otherwise indicated.

EXAMPLE 1

In Vitro Cerebrocortical Tissue Slice Assay

Adult cats of 2–3 kg body weight are employed in tissue slice studies. Prior to sacrifice, the animals are anesthetized with ketamine hydrochloride (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO^4$, 1.2; Hepes (N-2-hydroxyethylpiperazine-N'-2-ethanesulfonic acid, titrated with NaOH to pH 7.4), 20. Except when adding $HCO_3^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2$/97.5% $O_2$ instead of 100% $O_2$.

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO_3^-$-stimulated swelling that occurred in its presence, computed as a percent of the maximum possible. Tissue and media $Na^+$ and $K^+$ levels are determined by emission flame photometry with $Li^+$ internal standard; $Cl^-$ levels are determined by amperometric titration. Tissue viability during incubation is monitored by manometry.

EXAMPLE 2

[(1,2-Dichloro-8-oxo-5a-propyl-5a,6,7,8-tetrahydrodibenzofuran-3-yl)oxy]acetic acid

Step A: 3,4,5-Trichlorophenol, benzyl ether

A mixture of 3,4,5-trichlorophenol (8.0 g, 0.04 mole) benzyl bromide (7.5 g, 0.044 mole) and potassium carbonate (6.1 g, 0.044 mole) in N,N-dimethylformamide (DMF) (50 mL) was heated at 60° C. with stirring for 3 hours then poured into ice water. The 3,4,5-trichlorophenol benzyl ether was filtered rinsed with water, dried and used in Step B without further purification.

Step B: 2,3-Dichloro-5-benzyloxyanisole

A mixture of 3,4,5-trichlorophenol benzyl ether (7.5 g, 0.026 mole) and sodium methoxide (1.7 g, 0.032 mole) in hexamethylphosphoramide (60 ml) was heated with stirring on a steam bath for 20 hours. The reaction mixture was poured into ice water, extracted into ether, washed with water, brine, and dried over magnesium sulfate. The solvent was evaporated at reduced pressure and the residual oil chromatographed on silica gel (320 g) eluting with ethyl acetate-hexane; 1:4 to obtain 1.1 g of 2,3-dichloro-5-benzyloxyanisole which melted at 79°–81° C.

Analysis for $C_{14}H_{12}Cl_2O_2$: Calc: C, 59.38, H, 4.27; Found: C, 59.94; H, 4.25.

Step C: 3,4-Dichloro-5-methoxyphenol

To a solution of 2,3-dichloro-5-benzyloxyanisole (3.4 g, 0.02 mole) in acetic acid (60 ml) was added 5% palladium on carbon (2.0 g) and the mixture hydrogenated using a Parr apparatus at 20 p.s.i. of hydrogen for 3 hours. The catalyst was removed by filtration and the acetic acid evaporated at reduced pressure. The residue was dissolved in ether, extracted with 2N sodium hydroxide acidified, extracted into ether, washed with water, brine, dried over magnesium sulfate and the solvent removed by evaporation in vacuo to give 1.0 g of 3,4-dichlor-5-methoxyphenol which melted at 119°–120° C.

Analysis for $C_7H_6Cl_2O_2$: Calc: C, 43.55; H, 3.13; Found: C, 43.88; H, 3.12.

Step D: 2-(3,4-Dichloro-5-methoxy)phenoxypentanoic acid

A mixture of 3,4-dichloro-5-methoxyphenol (1.1 g, 0.0062 mole) potassium carbonate (0.95 g, 0.0068 mole) and ethyl 2-bromopentanoate (1.35 g, 0.0065 mole) in N,N-dimethylformamide (10 ml) was heated at 65° C. with stirring for 1 hour. To the reaction mixture was added water (10 ml) and 10N sodium hydroxide solution (2 ml) and heating was continued on a steam bath for 3 hours. The reaction mixture was poured into ice water, acidified with hydrochloric acid, extracted with ether, washed with water, brine, dried over $MgSO_4$ and evaporated at reduced pressure to give 1.7 g of 2-(3,4-dichloro-5-methoxy)phenoxypentanoic acid which melted at 141° C. after recrystallization from butyl chloride.

Analysis for $C_{12}H_{13}Cl_2O_4$: Calc: C, 49.33; H, 4.49; Found: C, 49.33; H, 4.87.

Step E: 4,5-Dichloro-6-methoxy-3-oxo-2-propylbenzo-furan

A solution of 2-(3,4-dichloro-5-methoxy)phenoxypentanoic acid (7.5 g, 0.027 mole) and thionyl chloride (12 g, 0.10 mole) in benzene (30 ml) was heated at reflux for 1 hour. The benzene and excess thionyl chloride were evaporated at reduced pressure and the residual acid chloride was dissolved in methylene chloride (60 ml), cooled to 5° C. and treated over ½ hour with aluminum chloride (3.5 g, 0.027 mole). The reaction mixture was stirred at 25° C. for 18 hours then heated at reflux for ½ hour. The methylene chloride was evaporated at reduced pressure, the residue treated with ice water, extracted with ether, washed with water, brine, dried over MgSO$_4$ and the solvent evaporated at reduced pressure. Chromatography on silica gel (175 g) with ethyl acetate-hexane; 1:4 gave 3.5 g of 4,5-dichloro-6-methoxy-3-oxo-2-propylbenzofuran which melted at 90°–92° C.

Analysis for $C_{12}H_{12}Cl_2O_3$: Calc: C, 52.38; H, 4.40; Found: C, 52.45, H, 4.45.

Step F:
1,2-Dichloro-3-methoxy-8-oxo-5a-propyl-5a,6,7,8-tetrahydrodibenzofuran

A solution of 4,5-dichloro-6-methoxy-3-oxo-2-propylbenzofuran (0.785 g, 0.0029 mole) in tetrahydrofuran (THF) (8 ml) was warmed to 40° C. and treated with 1,5-diazabicyclo[4.3.0]non-5-ene (DBN) (10 µl) and then with methyl vinyl ketone (2 ml) over a 10 minute period. The reaction mixture was heated at 55° C. for ½ hour during which time DBN (2 x 10 µl) was added. The THF was evaporated in vacuo, the residual oil dissolved in ether and ethyl acetate, washed with water, dried over MgSO$_4$ and evaporated in vacuo. The residual oil consisting of 4,5-dichloro-6-methoxy-3-oxo-2-(3-oxobutyl)-2-propylbenzofuran (0.81 g) was dissolved in ethanol (10 ml) and water (5 ml), treated with 5% NaOH (1 ml) and stirred at 25° C. for 72 hours. Treatment of the reaction mixture with water (5 ml) caused precipitation of 1,2-dichloro-3-methoxy-8-oxo-5a-propyl-5a,6,7,8,-tetrahydrodibenzofuran (0.6 g) which melted at 172°–173° C.

Analysis for $C_{16}H_{16}Cl_2O_3$: Calc: C, 58.73, H, 4.93; Found: C, 58.81; H, 5.07.

Step G:
1,2-Dichloro-3-hydroxy-8-oxo-5a-propyl-5a,6,7,8-tetrahydrodibenzofuran

A mixture of 1,2-dichloro-3-methoxy-8-oxo-5a-propyl-5a,6,7,8-tetrahydrodibenzofuran (0.6 g) and pyridine hydrochloride (7 g) was heated with stirring at 190° for ½ hour then poured into ice water. The solid which separated was filtered, rinsed with water, dried and used in Step H without further purification.

Step H:
[(1,2-Dichloro-8-oxo-5a-propyl-5a,6,7,8-tetrahydrodibenzofuran-3-yl)oxy]acetic acid A stirred mixture of 1,2-dichloro-3-hydroxy-8-oxo-5a-propyl-5a,6,7,8-tetrahydrodibenzofuran (0.4 g) potassium carbonate (0.2 g) and ethyl bromoacetate (200 µl) in N,N-dimethylformamide (7 ml) was heated at 65° C. for 1 ¼ hours. The reaction mixture was poured into ice water and the solid ester which precipitated was removed by filtration then dissolved in methanol (15 ml) containing water (1 ml) and 10N sodium hydroxide (1 ml). After ½ hour the methanol solution was poured into dilute aqueous hydrochloric acid, extracted with ether which was washed with water, brine, dried over MgSO$_4$ and evaporated in vacuo. Trituration of the residue with methylene chloride gave 0.35 g of (1,2-dichloro-8-oxo-5a-propyl-5a,6,7,8-tetrahydrodibenzofuran-3-yl)acetic acid which melted at 248°–250° C.

Analysis for $C_{17}H_{16}Cl_2O_5$: Calc: C, 55.00; H, 4.34; Found: C, 55.14; H, 4.48.

EXAMPLE 3

Resolution of [(1,2-Dichloro-8-oxo-5a-propyl-5a,6,7,8-tetrahydrodibenzofuran-3-yl)oxy]acetic acid Racemic [(1,2-dichloro-8-oxo-5a-propyl5a,6,7,8-tetrahydrodibenzofuran-3-yl)oxy]acetic acid (3.71 g, 10 mmole) in acetonitrile (270 ml) is heated to boiling and cinchonine (2.95 g, 10 mmole) is added. The solution is stirred at 5° C. for 48 hours and the solid (I) that separates removed by filtration, washed with acetonitrile and dried. The filtrate (II) is saved. The solid (I) is recrystallized from acetonitrile and the product removed by filtration, washed with acetonitrile, dried, treated with 1 normal hydrochloric acid (50 ml) and extracted with a solution of 20% tetrahydrofuran in ether. The extract is washed with brine dried over magnesium sulfate, the solvent evaporated in vacuo and the residue recrystallized from toluene to give the pure R-enantiomer of [(1,2-dichloro-8-oxo-5a-propyl-5a,6,7,8-tetrahydrodibenzofuran-3-yl)oxy]acetic acid.

Filtrate II is evaporated in vacuo, treated with 2N hydrochloric acid (45 ml), extracted with 20% tetrahydrofuran in ether, washed with brine and dried over magnesium sulfate. The solvent is evaporated in vacuo and the residue dissolved in acetonitrile (250 ml), heated to boiling and cinchonidine (2.95 g, 10 mMole) is added. The solution is cooled to 5° and stirred for 48 hours. The solid that separates is treated as described for I to obtain the pure S-enantiomer of [(1,2-dichloro-8-oxo-5a-propyl-5a,6,7,8-tetrahydrodibenzofuran-3-yl)oxy]acetic acid.

EXAMPLE 4

2-[(1,2-Dichloro-8-oxo-5a-propyl-5a,6,7,8-tetrahydrodibenzofuran-3-yl)oxy]ethaneimidamide hyd Step A:
2-[(1,2-DiChloro-8-oxo-5a-propyl-5a,6,7,8-tetrahydrodibenzofuran-3-yl)oxy]acetonitri A stirred mixture of 1,2-dichloro-3-hydroxy-8-oxo-5a-propyl-5a,6,7,8-tetrahydrodibenzofuran (0.4 g), potassium carbonate (0.2 g) and chloroacetonitrile (160 µl) in N,N-dimethylformamide (7 ml) is heated at 65° C. for 2 hours, poured into ice water, extracted with ether, washed with water, brine, dried over MgSO$_4$ and evaporated in vacuo. Trituration of the residual oil with butyl chloride gives 2-[(1,2-dichloro-8-oxo-5a-propyl-5a,6,7,8-tetrahydrodibenzouran-3-yl)oxy]acetonitrile which is filtered and dried.

Step B:
2-[(1,2-Dichloro-5a,6,7,8-tetrahydro-8-oxo-5a-propyl-5a,6,7,8-tetrahydrodibenzofuran-2-yl)oxy]ethaneimidamide hydrochloride To a solution of 2-[(1,2-dichloro-8-oxo-5a-propyl-5a,6,7,8-tetrahydrodibenzofuran-3-yl)oxy]acetonitrile (200 mg) in methanol (3 ml) is added sodium methoxide (10 mg). After stirring for 1 hour ammonium chloride (80 mg) is added and stirring is continued for 2 hours. The reaction mixture is poured into ice water containing 0.5 ml of 10N sodium hydroxide extracted with ether, washed with water dried over potassium carbonate, filtered and acidified with 10N ethanolic hydrochloric acid to precipitate 2-[(1,2-dichloro-8-oxo-5a-propyl-5a,6,7,8-tetrahydrodibenzofuranyl)oxy]ethaneimidamide hydrochloride.

EXAMPLE 5

Preparation of the two enantiomers of 2-[(1,2-dichloro-8-oxo-5a-propyl-5a,6,7,8-tetrahydrodibenzofura ethanimidamide hydrochloride Step A: R-1,2-Dichloro-3-hydroxy-8-oxo5a-propyl-5a,6,7,8,-tetrahydrodibenzofuran R-[(1,2-Dichloro-8-oxo-5a-propyl-5a,6,7,8-tetrahydrodibenzofuran-3-yl)oxy]acetic acid (Example 3) (1.86 g, 5 mmole) and pyridine hydrochloride (18.6 g, 160 mMole) is heated with stirring for 15 minutes at 185° C. and then poured into crushed ice. The solid R-1,2-dichloro-3-hydroxy-8-oxo-5a-propyl-5a,6,7,8-tetrahydrodibenzofuran that separates is separated by filtration, washed with water, dried and used in the next step without purification.

Step B: R-[(1,2-Dichloro-8-oxo-5a-propyl-5a,6,7,8-tetrahydrodibenzofuran-3-yl)oxy]acetonitrile By carrying out the reaction as described in Example 4, Step A, except that the racemic 1,2-dichloro-3-hydroxy-8-oxO-5a-propyl-5a,6,7,8-tetrahydro is replaced by R-1,2-dichloro-3-hydroxy-8-oxo-5a-propyl-5a,6,7,8-tetrahydrodibenzofuran there is obtained R-[(1,2-dichloro-8-oxo-5a-propyl-5a,6,7,8-tetrahydrodibenzofuran-3-yl)oxy]acetonitrile.

Step C: R-2-[(1,2-Dichloro-8-oxo-5a-propyl-5a,6,7,8-tetrahydrodibenzofuran-3-yl)oxy]ethanimid By carrying out the reaction as described in Example 4, Step B except that the racemic 2-[(1,2--dichloro-8-oxo-5a-propyl-5a,6,7,8-tetrahydrodib acetonitrile is replaced by R-2-[(1,2-dichloro-8-oxo-5a-propyl-5a,6,7,8-tetrahydrodibenzofuran-3-yl)oxy]acetonitrile there is obtained R-2-[(1,2-dichloro-8-oxo-5a-propyl-5a,6,7,8-tetrahydrodibenzofuran-3-yl)oxy]ethanimidamide hydrochloride.

By replacing the R-[(1,2-dichloro-8-oxo-5a-propyl-5a,6,7,8-tetrahydrodibenzofuran-3-yl)oxy]acetic acid used in Example 5, Step A with the corresponding S-enantiomer and using the product of that reaction in Step B and the product of Step B in Step C there is obtained S-[(1,2-dichloro-8-oxo-5a-propyl-5a,6,7,8-tetrahydrodibenzofuran-3-yl)oxy]ethanimidamide hy

EXAMPLE 6

1-Carboxy-1-methylethyl [(1,2-dichloro-8-oxo-5a-propyl-5a,6,7,8-tetrahydrodibenzofuran-3-

[(1,2-Dichloro-8-oxo-5a-propyl-5a-propyl-5a,6,7,8-,tetrahydrodibenzofuran-3-yl)oxy]acetic acid (3.71 g, 10 mmole) is dissolved in tetrahydrofuran (20 ml). 1,1'-Carbonyldiimidazole (3.2 g, 10 mmole) is added and the mixture stirred at 20° C. for one hour. 2-Hydroxy-2-methylpropionic acid (1.05 g, 10 mmole) is added and the mixture stirred for 18 hours at 25° C. The solvent is removed by evaporation in vacuo and the residue dissolved in methylene chloride, washed with water and dried over magnesium sulfate. The solvent is removed by evaporation in vacuo and the residue purified by column chromatography over silica (250 g) using a methylene chloride/tetrahydrofuran/acetic acid 100/2/1 (v.v.v.) mixture as the eluant. Selecting the appropriate fractions gave 1-carboxy-1-methylethyl [(1,2-dichloro-8-oxo-5a -propyl-5a,6,7,8-tetrahydrodibenzofuran-3-yl)oxy]acetate upon evaporation of the solvent.

By using a pure enantiomer (R- or S-) of [(1,2-dichloro-8-oxo-5a-propyl-5a,6,7,8-tetrahydrodibenzofuran-3-yl)oxy]acetic acid instead of the racemate, there is obtained the pure 1-carboxy-1-methylethyl R-[(1,2-dichloro-8-oxo-5a-propyl-5a,6,7,8-tetrahydrodibenzofuran-3-yl)oxy]acetate or 1-carboxy-1-methylethyl S-[(1,2-dichloro-8-oxo-5a -propyl-5a,6,7,8-tetrahydrodibenzofuran-3-yl)oxy]acetate.

EXAMPLE 7

Parenteral solution of the Sodium Salt of R-[(1,2-dichloro-8-oxo-5a-propyl-5a,6,7,8-tetrahydrodibenzofuran acetic acid The R-[(1,2-dichloro-8-oxo-5a-propyl5a,6,7,8-tetrahydrodibenzofuran-3-yl)oxy]acetic acid (Example 3) (500 mg) is dissolved by stirring and warming with a solution of 0.25N sodium bicarbonate (5.6 ml). The solution is diluted to 10 ml with water and sterilized by filtration. All the water that is used in the preparation is pyrogen-free. The concentration of the active ingredient (calculated as free acid) in the final solution is 5%.

Similar parenteral solutions can be prepared by replacing the active ingredient of this Example by any of the other carboxylic acids of this invention.

EXAMPLE 8

Parenteral solution of R-2-[(1,2-Dichloro-8-oxo-5a-propyl-5a,5,7,8-tetrahydrodibenzofuran-3-yl) hydrochloride The R-2-[(1,2-dichloro-8-oxo-5a-propyl5a,6,7,8-tetrahydrodibenzofuran-3-yl)oxy]ethanimidamide hydrochloride (Example 5) (549 mg) is dissolved by warming with sufficient water to give a total volume of 10 ml and the solution is sterilized by filtration. All the water used in the preparation is pyrogen-free. The concentration of the active ingredient (calculated as free base) is 5%.

Similar parenteral solutions can be prepared by replacing the active ingredient of this Example by any of the other imidamide salts of this invention.

EXAMPLE 9

Dry-Filled Capsules Containing 100 mg of Active Ingredient (free acid) Per Capsule

|  | Per Capsule |
|---|---|
| [(1,2-Dichloro-8-oxo-5a-propyl-5a,6,7,8-tetrahydrodibenzofuran-7-yl)oxy]-acetic acid | 100 mg |
| Lactose | 99 mg |
| Magnesium Stearate | 1 mg |
| Capsule (Size No. 1) | 200 mg |

The [(1,2-dichloro-8-oxo-5a-propyl-5a,6,7,8-tetrahydrodibenzofuran-3-yl)oxy]acetic acid (Example 2, Step H) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 10

Dry-Filled Capsules Containing 100 mg of Active Ingredient (free and) Per Capsule

|  | Per Capsule |
|---|---|
| 2-[(1,2-Dichloro-8-oxo-5a-propyl-5a,6,7,8-tetrahydrofuran-3-yl)oxy]ethanimidamide hydrochloride | 110 mg |
| Lactose | 89 mg |
| Magnesium Stearate | 1 mg |
| Capsule (Size No. 1) | 200 mg |

The 2-[(1,2-dichloro-8-oxo-5a-propyl-5a,6,7,8-tetrahydrodibenzofuran-3-yl)oxy]ethanimidamide hydrochloride (Example 4, Step B) is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 11

Dry-Filled Capsules Containing 100 mg of Active Ingredient (ester) Per Capsule

|  | Per Capsule |
|---|---|
| 1-Carboxy-1-methylethyl [(1,2-dichloro-8-oxo-5a,6,7,8,tetrahydrodibenzofuran-3-yl)oxy]-acetate | 100 mg |
| Lactose | 99 mg |
| Magnesium Stearate | 1 mg |
| Capsule (Size No. 1) | 200 mg |

The 1-carboxy-1-methylethyl [(1,2-dichloro8-oxo-5a-propyl-5a,6,7,8,tetrahydrodibenzofuran-3-yl)oxy]acetate (Example 6) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of this Example by any of the other compounds of this invention.

What is claimed is:

1. A compound of the formula:

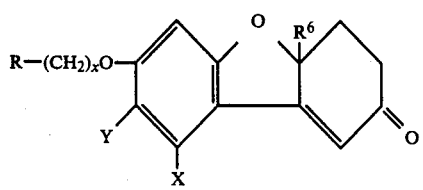

(I)

wherein:
R is

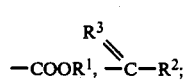

$R^1$ is hydrogen, $C_1$-$C_6$ alkyl, $C_1$-$C_6$ carboxyalkyl;
$R^2$ is $NH_2$, $NHR^4$ or $NR^4R^5$;
$R^3$ is NH or $NH^4$;
$R^4$ and $R^5$ are each independently lower alkyl, branched or unbranced, containing from 1 to 5 carbon atoms, or amino, provided that $R^4$ and $R^5$ are not both amino;

wherein $R^2$ and $R^3$ may be joined together via $R^4$ to form a heterocyclic ring of 5 or 6 atoms containing 2 nitrogen atoms and 3 or 4 carbon atoms, or wherein $R^4$ and $R^5$ may be joined together to form a 5- or 6-membered ring containing one nitrogen atom and 4 or 5 carbon atoms $R^6$ is lower alkyl, branched or unbranched, containing from 1 to 5 carbon atoms, phenyl, p-fluorophenyl, o-fluorophenyl, p-chlorophenyl, benzyl, cycloalkyl containing from 3 to 6 nuclear carbon atoms, or cycloalkyl-lower alkyl containing from 4 to 7 total carbon atoms;

X and Y are halo or lower alkyl; and
x is 1 to 4.

2. A compound of the formula:

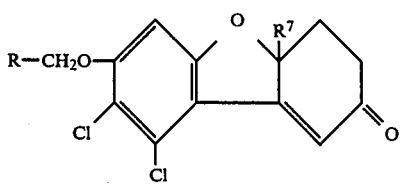

(II)

wherein:
R is carboxy,

$R^7$ is lower alkyl, branched or unbranched, containing from 1 to 5 carbon atoms.

3. A compound of claim 1, which is [(1,2-dichloro-8-oxo-5a-propyl-5a,6,7,8-tetrahydrodibenzofuran-3-yl)oxy]acetic acid.

4. A compound of claim 3, which is the (+)-enantiomer.

5. A compound of claim 3, which is the (−)-enantiomer.

6. A compound of claim 1, which is 1-carboxy-1-methylethyl [(1,2-dichloro-8-oxo-5a-propyl-5a,6,7,8-tetrahydrodibenzofuran-3-yl)oxy]-acetate.

7. A compound of claim 6, which is the (+)-enantiomer.

8. A compound of claim 6, which is the (−)-enantiomer.

9. A compound of claim 1, which is 2-[(1,2-dichloro-8-oxo-5a-propyl-5a,6,7,8-tetrahydrodibenzofuran-ethanimidamide hydrochloride.

10. A compound of claim 9, which is the (+)-enantiomer.

11. A compound of claim 9, which is the (−)-enantiomer.

12. A pharmaceutical composition useful in the treatment of brain injury comprising a pharmaceutical carrier and an effective amount of a compound of claim 1.

13. A method of treating a person with brain injury which comprises administering to such a person an effective amount of a compound of claim 1.

* * * * *